United States Patent [19]

Jones

[11] 4,404,135
[45] Sep. 13, 1983

[54] ENKEPHALIN DERIVATIVES

[75] Inventor: David A. Jones, Evanston, Ill.

[73] Assignee: G. D. Searle & Co., Skokie, Ill.

[21] Appl. No.: 405,975

[22] Filed: Aug. 9, 1982

Related U.S. Application Data

[63] Continuation-in-part of Ser. No. 284,428, Jul. 20, 1981, abandoned.

[51] Int. Cl.³ ........................................... C07C 103/52
[52] U.S. Cl. ............................................. 260/112.5 E
[58] Field of Search ................................. 260/112.5 E

[56] References Cited

U.S. PATENT DOCUMENTS 4,273,704  6/1981  Mazur .......................... 260/112.5 E Primary Examiner—Delbert R. Phillips
Attorney, Agent, or Firm—James G. Passe

[57] ABSTRACT

The invention relates to novel enkephalin derivatives which are useful as analgesic agents of the formula:

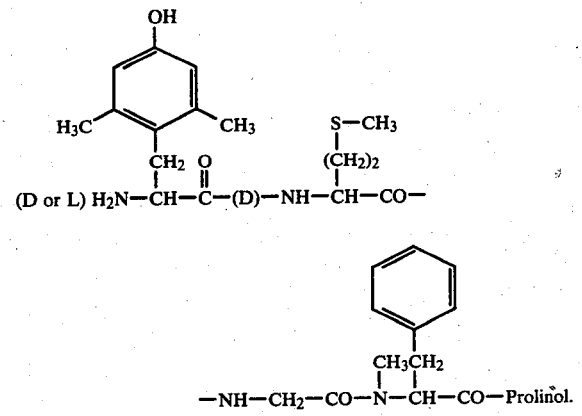

2 Claims, No Drawings

ENKEPHALIN DERIVATIVES

BACKGROUND OF THE INVENTION

This application is a continuation-in-part-of-application Ser. No. 06/284,428 filed July 20, 1981, now abandoned.

The present invention relates to novel enkephalin derivatives. In particular, it provides novel enkephalin derivatives of formula I which are useful as analgesic agents. It has also been discovered that these compounds are also useful as antihypertensives.

In 1975, a pentapeptide, methionine enkephalin, was reported by Hughes et al. *Nature*, 258, p577 (1975). This peptide is found in many areas of the brain where it appears to act as a neurotransmitter of neuromodulator in a central pain-suppressant system. The natural peptide binds stereospecifically to partially purified brain opiate receptor sites, see for example, Bradberry et al., *Nature*, 260, p793(1976). The natural peptide is also highly active in bioassays for opiate activity but exhibits only weak, fleeting analgesic activity when injected directly into the brain of the rat, see for example, Belluzi et al., *Nature*, 260, 625 (1976).

In order to overcome the lack of in vivo activity, a number of investigators have made numerous modifications in the methionine enkephalin structure, such as substituting the glycine in the 2-position with a D-amino acid, N-methylation of the L-tyrosine, substituting the 4-phenylalanine with, for example methyl or halo, modifying the C-terminus, etc. to produce enkephalin derivatives of varying properties and potencies. The present invention provides new enkephalin derivatives which approach the potency of morphine as analgesic agents by both oral and parenteral routes of administration.

SUMMARY OF THE INVENTION

The present invention particularly provides enkephalin derivatives according to Formula I. Formula II shows the structure of prolinol. The analgesic activity for the compounds of the present invention was established in the hot-plate assay and mouse PBQ-writhing assay, and the analgesic activity of the representative compounds was compared with that of morphine.

By virtue of the analgesic activity, the compounds of Formula I are useful in treating symptoms in humans and animals. A physician or veterinarian of ordinary skill could readily determine a subject who is exhibiting such symptoms. Regardless of the route of administration selected, the compounds of the present invention are formulated into pharmaceutically acceptable dosage forms by conventional methods known to the pharmaceutical art. The compounds can be administered in such oral dosage forms as tablets, capsules, pills, powders, granules, suspensions, or solutions. They may also be administered rectally or vaginally, in such forms as suppositories or bougies. They may also introduced in the form of eyedrops, interparenterally, subcutaneously or intramuscularly, using forms known to the pharmaceutical art. In general the preferred form of administration is oral.

An effective but nontoxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration of the particular compound employed. An ordinary skilled physician or veterinarian will readily determine and prescribe the effective amount based on the route of administration of the analgesic agent to prevent or arrest the progress of the condition. In so proceeding, the physician or veterinarian could employ relatively low dosages at first, subsequently increasing the dose until a maximum response is obtained.

The compounds of Formula I can also be administered as pharmacologically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The invention will appear more fully from the examples which follow. These examples are given by way of illustration only, and are not to be construed as limiting the invention either in spirit or in scope, as many modifications both in materials and in methods will be apparent from this disclosure to those skilled in the art.

DESCRIPTION OF THE PREFERRED EMBODIMENTS

Example I

A solution of 3.25 g (7.23 mmol) of (DL)(BOC-2,6-diMe-Tyr(D)-Met-OH, 1.00 gram (8.7 mmol) of HOSu and 1.79 grams (8.70 mmol) of DCCD in 18 ml of DMF is stirred at room temperature for two and one-half hours and then refrigerated overnight. To the reaction mixture is added 2.43 grams (8.70 mmol) of H-Gly-Me-Phe-OH.HCL and 1.00 ml of N-methyl-morpholine in 10 ml of DMF. The reaction mixture is stirred for six hours at room temperature and then is refrigerated overnight. The DCU is filtered from the reaction mixture and the filtrate is added to the 350 ml of cold, 5 percent of potassium sulfate to give white precipitate. This is filtered, washed with water, and dried thoroughly to give 4.44 grams (93 percent) of a tetrapeptide. 2.03 grams (3.00 mmol) of the tetrapeptide is dissolved in the 0.34 ml (3.06 mmol) of N-methylmorpholine (NMM) in 15 ml of DMF and cooled to minus 28° C. To this solution is added 0.42 ml (3.17 mmoles) of

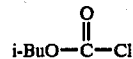

rapidly. After 45 seconds, a white precipitate of NMM HCL forms. After stirring for 20 minutes at minus 25° C., 0.33 grams (3.3 mmoles) of (L)-prolinol in two ml of DMF is added over a 5-minute period. The reaction mixture is stirred for 50 minutes at minus 30° C., then allowed to warm to room temperature and stand for 48 hours, after which it is added to 250 ml of cold 5 percent potassium bisulfate. A precipitate forms which is filtered, washed with water, and then dried in vacuo at 30° C. for 1½ hours and at 45° C. degree for about 5 hours. This yields a crude pentapeptide alcohol 1.79 grams (80.6 percent).

Purification is obtained by means of low-pressure liquid chromatography. Fractions 7 through 11 produce 354 mg; fractions 14 through 24 produce 205 mg for a total of 25.2 percent of the total starting material. 55.2 percent of the total starting material is recovered as BOC-tetrapeptide.

Fractions 7 through 11 and 14 through 24 were identical by NMR spectroscopy and the spectra confirmed the BOC proctected prolinol structure. These represented the two diasteroisomers, (L)2,6-diMeTyr and (D)2,6-diMeTyr.

Example II

Fractions 7 through 11 of the BOC-protected prolinol compound (approximately 0.48 mmoles) of Example I is deblocked with 0.8 ml of 5.6 N HCL in dioxane after dissolving in 1.6 ml of dioxane. After standing 1 hour at room temperature, the solvent is evaporated with a water pump and ether is added to the resulting oil. A precipitate forms which is filtered, washed with ether, and dried in vacuo at 55° C. for 3 hours to yield 258 mg or 79 percent. The structure was confirmed by NMR.

Example III

Fractions 14 through 21 of the BOC-protected prolinol compound of Example I (Approximately 0.28 mmoles) is treated in the same manner as described in Example I except using 0.5 ml of HCL and dioxane after solution in 0.9 ml dioxane. The yield is 126 mg (66 percent). The structure is as confirmed by NMR.

Chart A

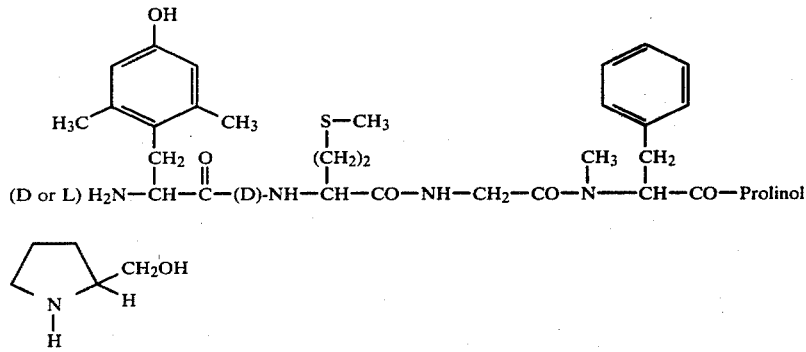

I claim:
1. 1-[N-[N-[N-(2,6-dimethyl-D-tyrosyl)-D-methionyl]glycyl]-N-methyl-L-phenylalanyl]-2-pyrrolidinemethanol, monohydrochloride
2. 1-[N-[N-[N-(2,6-dimethyl-L-tyrosyl)-D-methionyl]glycyl]-N-methyl-L-phenylalanyl]-2-pyrrolidinemethanol, monohydrochloride.

* * * * *